US00PP08579P

United States Patent [19]

Warriner, deceased

[11] Patent Number: Plant 8,579

[45] Date of Patent: Feb. 8, 1994

[54] FLORIBUNDA ROSE PLANT NAMED 'JACDOR'

[75] Inventor: William A. Warriner, deceased, late of Tustin, Calif. by Alene B. Warriner, legal representative

[73] Assignee: Bear Creek Gardens, Inc., Medford, Oreg.

[21] Appl. No.: 883,280

[22] Filed: May 14, 1992

[51] Int. Cl.[5] ..... A01H 5/00

[52] U.S. Cl. ..... Plt./22

[58] Field of Search ..... Plt. 22, 28, 11, 12

*Primary Examiner*—Howard J. Locker

*Attorney, Agent, or Firm*—Klarquist, Sparkman, Campbell, Leigh and Whinston

[57] ABSTRACT

A floribunda rose having bright red with yellow reverse flowers of high centered hybrid tea flower form, long vase life, and many small prickles on main stems and glands on peduncles.

1 Drawing Sheet

1

The present invention relates to a new and distinct variety of rose plant of the Floribunda class which was originated by me by crossing the variety of an unnamed seedling, with the variety KORfarim, U.S. Plant Pat. No. 3,229.

The primary objective of this breeding was to produce a new rose variety having a flower color similar to the male parent KORfarim but with the more compact floribunda habit and dense foliage of the female unnamed seedling floribunda. The objective was substantially achieved along with other desirable improvements as evidenced by the following unique combination of characteristics which are outstanding in the new variety and which distinguish it from its parents, as well as from all other varieties of which I am aware:

1. Bright red with bright yellow reverse flowers;
2. High centered hybrid tea form in a floribunda rose;
3. Long vase life for a garden floribunda rose;
4. Very glandular peduncle;
5. Many small prickles on main wood of the plant.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—KORfarim, U.S. Plant Pat. No. 3,229.

Classification:

*Botanical.*—Rosa hybrida.

*Commercial.*—Floribunda.

2

FLOWER

Observations made from specimens grown in a garden environment in Somis, Calif. from Aug.-Oct. of 1991.

Blooming habit: Recurrent.

Bud:

*Size.*—1" when the petals start to unfurl.

*Form.*—Short, pointed ovoid.

*Color.*—When sepals first divide, bud color is Red Group 44A on the petal tips with the rest of the petal Yellow Group 10C. When half blown, the upper sides of the petals are Red Group 44A; and the lower sides of the petals are Yellow Group 10C.

*Sepals.*—Color: Green Group 138B. Surface texture: Covered in fine hairs. There are three normal to heavily appendaged sepals. There are two unappendaged sepals with hairy edges.

*Receptacle.*—Color: Green Group 138B. Shape: Funnel. Size: Small, $\frac{1}{4}'' \times \frac{1}{4}''$. Surface: Smooth.

*Peduncle.*—Length: Short, 2". Surface: Glandular. Color: Medium green. Strength: Stiff, erect.

Bloom:

Size.—Medium. Average open size is $3\frac{1}{2}''$.

*Borne.*—Singly and in clusters. If in clusters: flat.

*Stems.*—Medium, strong, 14".

*Form.*—When first open: High centered. Permanence: Retains its form to the end, outer petals curl back.

*Petalage.*—Number of petals under normal conditions: 25-30.

*Color.*—The upper side of the petals is Red Group 44A. The reverse side of the petals is Yellow Group 10C. The base of the petals are a distinctive yellow having a half moon (Yellow Group 13C) about $\frac{3}{8}'' \times \frac{3}{8}''$. The major color on the upper side is Red Group 44A.

*Variegations.*—Occasional white streak on the guard petals.

*Discoloration.*—The general tonality at the end of the first day: No change. At the end of the third day: No change.

*Fragrance.*—Slight.

Petals:

*Texture.*—Thick.

*Shape.*—Deltoid.
*Form.*—Tips slightly recurved, moderately quilled.
*Arrangement.*—Imbricated with few petaloids in the center.
*Persistence.*—Hang on and dry.
*Lastingness.*—On the plant: Long, 7 days. As a cut flower: Long, 7-8 days.

Reproductive parts:
*Anthers.*—Size: Medium. Quantity: Many. Color: Yellow. Arrangement: Regular around styles.
*Filaments.*—Color: Yellow.
*Pollen.*—Color: Yellow.
*Styles.*—Color: Red.
*Stigmas.*—Color: Yellow.

Form: Bush.

Growth: Vigorous; medium; upright; branching.

Foliage: Number of leaflets on normal mid-stem leaves: 5 or 7.
*Size.*—Medium, 5″×3″.
*Quantity.*—Abundant.
*Color.*—New foliage: Reddish. Old foliage: Dark green.

Leaflets:
*Shape.*—Pointed oval.
*Texture.*—Upper side: Leathery, glossy.
*Edge.*—Serrated.
*Serration.*—Single, small.

*Petiole rachis.*—Color: Green.
*Petiole underside.*—Rough with prickles.
*Stipules.*—Medium, serrated.
*Disease resistance.*—Susceptible to mildew but resistant to rust under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Medium, hooked downward.
*Color when young.*—Red.

Small prickles:
*Quantity.*—On main stalks: Many. On laterals: Few.
*Color.*—Brown.

I claim:

1. A new and distinct variety of rose plant of the floribunda class, substantially as herein shown and described, characterized particularly as to novelty by the unique combination of its bright red with light yellow reverse flowers, its high centered hybrid tea flower form, its long vase life and its many small prickles on main stems and glands on peduncles.

* * * * *

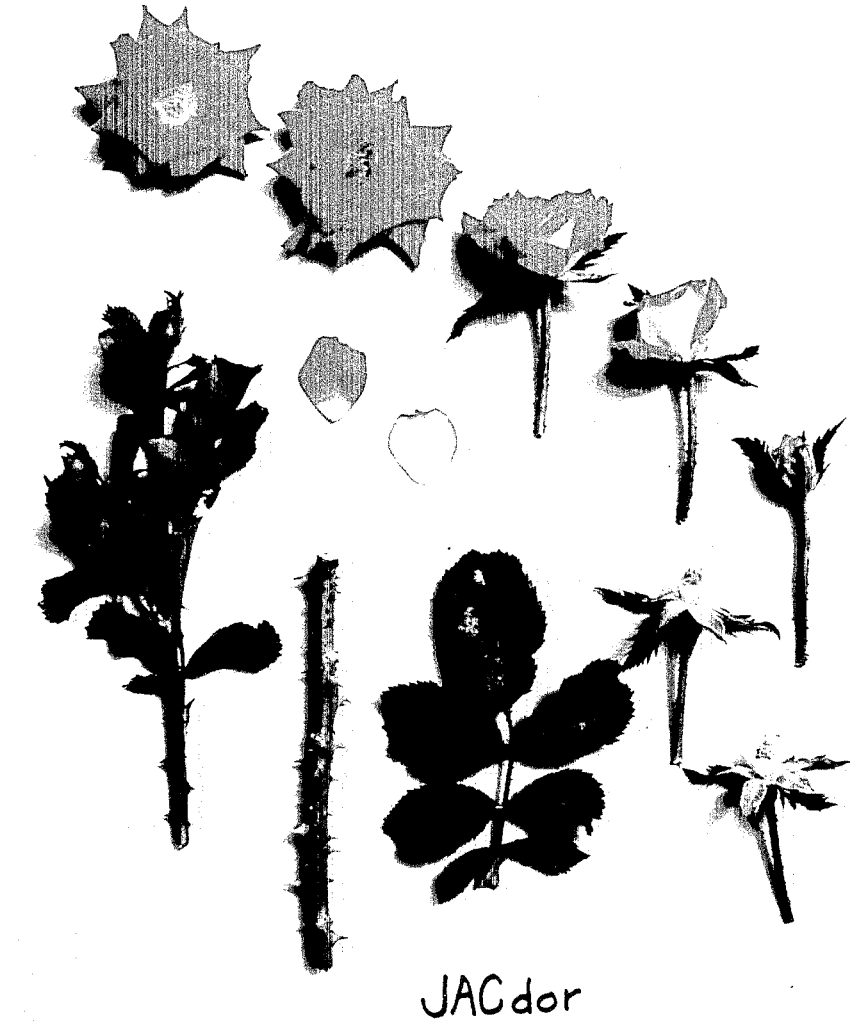
JACdor